United States Patent [19]
Whittemore et al.

[11] Patent Number: 6,034,081
[45] Date of Patent: *Mar. 7, 2000

[54] POTENTIATION OF BIOCIDE ACTIVITY USING AN N-ALKYL HETEROCYCLIC COMPOUND

[75] Inventors: Marilyn S. Whittemore, Germantown; Daniel E. Glover, Brighton; S. Rao Rayudu, Germantown, all of Tenn.

[73] Assignee: Buckman Laboratories International Inc, Memphis, Tenn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/453,001

[22] Filed: May 30, 1995

[51] Int. Cl.$^7$ .............................. A01N 43/00; A01N 47/00
[52] U.S. Cl. ........................ 514/231.2; 514/212; 514/315; 514/372; 514/376; 514/396; 514/408; 514/424; 514/479; 514/373; 514/626; 514/737; 514/738
[58] Field of Search .................................. 514/231.2, 396, 514/183, 315, 376, 408, 424, 372, 373, 479, 626, 737, 738

[56] References Cited

U.S. PATENT DOCUMENTS

| | | | |
|---|---|---|---|
| 3,923,870 | 12/1975 | Singer ..................................... | 260/482 |
| 4,173,643 | 11/1979 | Law ........................................ | 424/270 |
| 4,661,503 | 4/1987 | Martin et al. ............................ | 514/372 |
| 4,945,109 | 7/1990 | Rayudu ................................... | 514/478 |
| 5,182,277 | 1/1993 | Strumpf et al. ....................... | 514/231.2 |
| 5,219,875 | 6/1993 | Sherba et al. .......................... | 514/373 |
| 5,250,194 | 10/1993 | Hollis et al. ........................... | 210/764 |
| 5,328,926 | 7/1994 | Oppong .................................. | 514/372 |

FOREIGN PATENT DOCUMENTS

| | | |
|---|---|---|
| 2 184 945 | 7/1987 | United Kingdom . |
| 93/24008 | 12/1993 | WIPO . |
| 9419027 | 9/1994 | WIPO . |
| 94/26111 | 11/1994 | WIPO . |

OTHER PUBLICATIONS

Nachtigall et al., Arch. Phytopathol. Pflanzenenshutz (1991), 27 (1), 25–31 (abstract).

Bach et al., Seifen, Oele, Fette, Wachse (1990), 116/9) 345–55 (abstract).

BUSAN® 1078 product literature, 1 page, 1992.

Myacide® preservatives technical data sheet, 4 pages, 1990.

Busan® 94 product literature, 1 page, 1992.

Great Lakes Chemical, Material Safety Data Sheet, 4 pages, 1986.

*Primary Examiner*—Phyllis G. Spivack
*Attorney, Agent, or Firm*—Morgan, Lewis & Bockius LLP

[57] ABSTRACT

A method for increasing the effectiveness of a microbicide is described, wherein a microbicide and an N-alkyl heterocyclic compound are applied to a substrate or aqueous system subject to the growth of microorganisms. The N-alkyl heterocyclic compound is applied in an amount effective to increase the microbicidal activity of the microbicide. The N-alkyl heterocyclic compound has the formula:

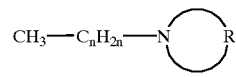

The variable "In" ranges from 5 to 17, and the heterocyclic ring defined by

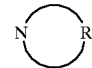

is a substituted or unsubstituted ring having four to eight members. Microbicidal compositions are described where the microbicide and the N-alkyl heterocyclic compound are present in a combined amount effective to control the growth of at least one microorganism. Methods for controlling the growth of microorganisms on various substrates and in various aqueous systems are also described. The combination of the microbicide and the N-alkyl heterocyclic compound is particularly useful as a microbicide in the leather industry, the lumber industry, the papermaking industry, the textile industry, the agricultural industry, and the coating industry, as well as in industrial process waters.

19 Claims, No Drawings

POTENTIATION OF BIOCIDE ACTIVITY USING AN N-ALKYL HETEROCYCLIC COMPOUND

BACKGROUND OF THE INVENTION

1. Field of the Invention

The present invention relates to compositions and methods for controlling the growth of microorganisms on a variety of substrates and in aqueous systems. More particularly, the invention relates to a combination of a microbicide with an N-alkyl heterocyclic compound where the N-alkyl heterocyclic compound potentiates the microbicide's microbicidal effect.

2. Background of the Invention

A large variety of commercial, industrial, agricultural, and wood materials or products are subject to microbiological attack or degradation which reduces or destroys their economic value. Examples of such materials or products include surface coatings, lumber, seeds, plants, leather and plastics. The various temperatures at which such materials or products are manufactured, stored, or used as well as their intrinsic characteristics make them susceptible to growth, attack, and degradation by common microorganisms such as algae, fungi, yeasts, and bacteria. These microorganisms may be introduced during a manufacturing or other industrial process, by exposure to air, tanks, pipes, equipment, and humans. They can also be introduced while using a material or product, for example, by multiple openings and reclosures of packages or from stirring or removing material with contaminated objects.

Aqueous systems are also highly subject to microbiological growth, attack, and degradation. These aqueous systems may be fresh, brackish or saltwater systems. Exemplary aqueous systems include, but are not limited to, latexes, surfactants, dispersants, stabilizers, thickeners, adhesives, starches, waxes, proteins, emulsifying agents, cellulose products, metal working fluids, cooling water, waste water, aqueous emulsions, aqueous detergents, coating compositions, paint compositions, and resins formulated in aqueous solutions, emulsions or suspensions. These systems frequently contain relatively large amounts of water and organic material causing them to be environments well-suited for microbiological growth and thus attack and degradation.

Microbiological degradation of aqueous systems may manifest itself as a variety of problems, such as loss of viscosity, gas formation, objectionable odors, decreased pH, emulsion breaking, color change, and gelling. Additionally, microbiological deterioration of aqueous systems can cause fouling of the related water-handling system, which may include cooling towers, pumps, heat exchangers, and pipelines, heating systems, scrubbing systems, and other similar systems.

Another objectionable phenomenon occurring in aqueous systems, particularly in aqueous industrial process fluids, is slime formation. Slime formation can occur in fresh, brackish or salt water systems. Slime consists of matted deposits of microorganisms, fibers and debris. It may be stringy, pasty, rubbery, tapioca-like, or hard, and may have a characteristic undesirable odor that is different from that of the aqueous system in which it formed. The microorganisms involved in its formation are primarily different species of spore-forming and nonspore-forming bacteria, particularly capsulated forms of bacteria which secrete gelatinous substances that envelop or encase the cells. Slime microorganisms also include filamentous bacteria, filamentous fungi of the mold type, yeast, and yeast-like organisms. Slime reduces yields in production and causes plugging, bulking, and other problems in industrial water systems.

Various chemicals known as microbicides have been used to prevent microbiological deterioration of industrial systems, raw materials, and products. Examples of such microbicides include:

Kathon: a two component microbicide mixture of 5-chloro-2-methyl-4-isothiazolin-3-one (CMI) and 2-methyl-4-isothiazolin-3-one (MI). Kathon is a broad spectrum microbicide used in the pulp and paper industry. Kathon is also recommended to control bacteria and fungi in water-based paper coatings and coating components. Kathon is available from Rohm and Haas, Philadelphia Pa. and as Busan® 1078 from Buckman Laboratories, Memphis Tenn. Busan® 1078 is contains 1.15% by weight of CMI and 0.35% by weight of MI as active ingredients. CMI and MI have the following chemical structures:

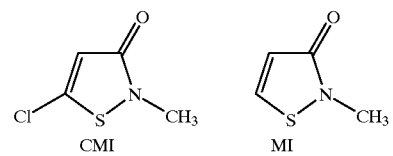

Bronopol: 2-bromo-2-nitropropane-1,3-diol. Bronopol is available as MYACIDE® from ANGUS Chemical Company, Northbrook Ill. Bronopol is used in water treatment, oil production fluids, waste injection wells, and with pulp and paper. The chemical formula of bronopol is:

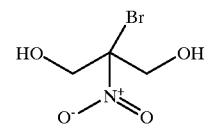

IPBC: Iodopropargyl butyl carbamate. IPBC can be obtained from Troy Chemical, Newark, N.J. IPBC is an effective fungicide, particularly in surface coating compositions, such as paint formulations. IPBC is disclosed in U.S. Pat. Nos. 3,923,870 and 5,219,875. IPBC has the following chemical formula:

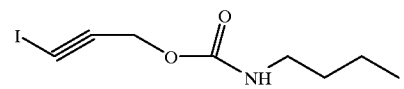

IPC: Iodopropargyl carbamate. IPC, an effective microbicide in aqueous systems and on numerous substrates, is disclosed in U.S. Pat. Nos. 4,945,109 and 5,328,926. The chemical formula of IPC is:

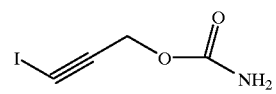

DBNPA: 2,2-Dibromo-3-nitrilopropionamide. DBNPA is available from Buckman Laboratories, Memphis, Tenn. as the product Busan® 94. DBNPA is a broad spectrum bactericide having particular use to control slime in the pulp and paper industry. Busan® 94 contains 20% by weight of DBNPA as its active ingredient. DBNPA has the chemical structure:

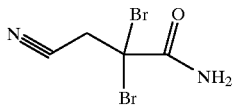

Tribromophenol: 2,4,6-Tribromophenol. Tribromophenol is an antifungal agent available from Great Lakes Chemical, West Lafayette, Ind. under the trade name GREAT LAKES PH-73. The chemical formula of tribromophenol is:

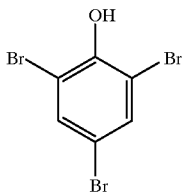

BIT: 1,2-benzisothiazoline-3-one. 1,2-Benzisothiazoline-3-one is a biocide useful for a variety of aqueous systems, such as metalworking fluids, paint, adhesives, starch-based-products, cellulose ether solutions, resin and rubber emulsions. 1,2-benzisothiazoline-3-one is available from ICI Specialty Chemicals, Melbourne, Australia as the product Proxel GXL-20, an aqueous solution of dipropylene glycol 20% by weight of 1,2-benzisothiazoline-3-one as the active ingredient. 1,2-Benzisothiazoline-3-one has the following chemical structure:

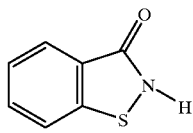

Despite the existence of such microbicides, industry is constantly seeking more cost-effective technology which offers equal or better protection at lower cost and lower concentration. The concentration of conventional microbicides and the corresponding treatment costs for such use, can be relatively high. Important factors in the search for cost-effective fungicides include the duration of microbicidal effect, the ease of use and the effectiveness of the microbicide per unit weight.

SUMMARY OF THE INVENTION

In view of industry's search for more cost effective microbicides, the present invention offers an improvement over current products or practices.

The present invention relates to a method to increase the effectiveness of a microbicide. This method applies a microbicide and an N-alkyl heterocyclic compound to a substrate or aqueous system subject to the growth of microorganisms. The N-alkyl heterocyclic compound is applied in an amount effective to increase the microbicidal activity of the microbicide. The N-alkyl heterocyclic compound has the formula:

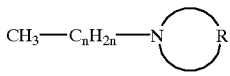

For the N-alkyl heterocyclic compound, n may vary from 5 to 17 and the heterocyclic ring defined by

is a substituted or unsubstituted ring having four to eight members. The combination of the microbicide with an N-alkyl heterocyclic compound achieves superior microbicidal activity at lower concentrations and lower cost than the microbicide alone against microbiological attack or degradation such as discussed above.

One embodiment of the invention provides a microbicidal composition. The composition contains (a) at least one microbicide and (b) an N-alkyl heterocyclic compound of the above formula. In the composition, the microbicide (a) and the N-alkyl heterocyclic compound (b) are present in a combined amount effective to control the growth of at least one microorganism.

Another embodiment of the present invention provides a method for controlling the growth of a microorganism on a substrate. This method contacts a substrate susceptible to the growth of microorganisms with at least one microbicide and an N-alkyl heterocyclic compound, having the above formula. The microbicide and N-alkyl heterocyclic compound are present in a combined amount effective to control the growth of at least one microorganism on the substrate.

Another embodiment of the invention provides a method for controlling the growth of microorganisms in an aqueous system capable of supporting growth of a microorganism. This method treats the aqueous system with at least one microbicide and an N-alkyl heterocyclic compound described above. The microbicide and the N-alkyl heterocyclic compound are present in a combined amount effective to control the growth of at least one microorganism in the aqueous system.

The combination of a microbicide and an N-alkyl heterocyclic compound according to the invention is useful in preventing the microbiological attack, degradation, or deterioration of various types of raw materials and products such as leather, textiles, pulp, paper and paperboard, coatings, lumber, as well as agricultural products such as seeds and crops. Advantageously, the combination may be used in various industrial processes used to prepare or manufacture these products. Accordingly, additional embodiments of the present invention employ the combination to control the growth of microorganisms on or in such industrial products, raw materials or processes.

The foregoing and other features and advantages of the present invention will be made more apparent from the following detailed description and preferred embodiments.

DETAILED DESCRIPTION OF THE INVENTION

The present invention relates to a method to increase the effectiveness of a microbicide. This method applies a microbicide and an N-alkyl heterocyclic compound to a substrate or aqueous system subject to the growth of microorganisms. The N-alkyl heterocyclic compound is applied in an amount effective to increase the microbicidal activity of the microbicide.

According to the invention, the combination of a microbicide and an N-alkyl heterocyclic compound demonstrates an unexpected, enhanced microbicidal effect. That is, the combination of a microbicide and an N-alkyl heterocyclic compound achieves superior microbicidal activity at lower microbicide concentrations as compared to the microbicidal capability of the microbicide alone. Thus, the N-alkyl heterocyclic compound potentiates, or even synergistically enhances, the microbicidal activity of the microbicide. Such a superior effect presents a distinct economic advantage and increases an individual microbicide's effectiveness per unit weight.

According to the invention, an N-alkyl heterocyclic compound may be used to increase the effectiveness of any microbicide or a mixture of microbicides. Preferred microbicides include 5-chloro-2-methyl-4-isothiazolin-3-one, 2-methyl-4-isothiazolin-3-one, 2-bromo-2-nitropropane-1, 3-diol, iodopropargyl butyl carbamate, iodopropargyl carbamate, 2,2-dibromo-3-nitrilopropionamide, tribromophenol, and 1,2-benzisothiazoline-3-one, and mixtures thereof. The N-alkyl heterocyclic compound, or a mixture of N-alkyl heterocyclic compounds, may be used with and in the same manner as the particular microbicide is used. Preferably, one or more N-alkyl heterocyclic compounds are incorporated into the formulation of the microbicide.

In one embodiment, the present invention relates to a microbicidal composition comprising at least one microbicide and an N-alkyl heterocyclic compound. The microbicide and the N-alkyl heterocyclic compound are present in a combined amount effective to control the growth of at least one microorganism.

The N-alkyl heterocyclic compounds employed in the present invention have the following general formula:

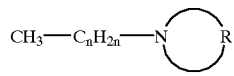

The variable "n" may vary from 5 to 17, and preferably from 9 to 15. Most preferably, n is 11. The alkyl chain defined by $CH_3C_nH_{2n}-$ may be branched or unbranched. Branched alkyl chains may lose some of their solubility in water or other aqueous systems. Unbranched alkyl groups are generally preferred.

The heterocyclic ring defined by

may have four to eight members and is preferably a five-, six-, seven-, or eight-member ring. Most preferably the heterocyclic ring is a six-membered ring.

Although the heterocyclic ring always contains one nitrogen atom, the remainder is generally a carbocycle. However, the ring may contain one or more additional heteroatoms selected from N, O, or S. The ring may be saturated or unsaturated. The ring may also have common substituents such as alkyl groups, substituted alkyl groups, alkenyl groups, substituted alkenyl groups, amino groups, an oxo group to form a cyclic ketone, halogens, etc. The heterocyclic ring may also be part of a multiple ring structure.

The heterocycles listed below exemplify substituted or unsubstituted heterocyclic rings which may be used in the N-alkyl heterocyclic compounds utilized in preferred embodiments of the present invention. Examples of five-membered heterocyclic rings include, but are not limited to, pyrrolidinyl, 2-pyrrolidinonyl, pyrrolinyl, pyrazolidinyl, pyrazolinyl, pyrazolyl, imidazolidinyl, imidazolinyl, imidazolyl and oxazolidinyl. Six-membered rings include, but are not limited to, piperidinyl, piperazinyl, and morpholinyl. Seven- and eight-membered rings such as hexamethyleneiminyl and heptamethyleneiminyl may also be used in the present invention. One of ordinary skill will appreciate that other heterocyclic rings may also be used.

N-alkyl heterocyclic compounds useful in the invention are available either commercially from chemical supply houses or may be prepared from starting materials using well-known literature methods. U.S. Pat. No. 5,250,194 discloses exemplary methods and is incorporated herein by reference.

U.S. Pat. No. 5,250,194 also describes N-dodecyl heterocyclic compounds and their use as microbicides for aqueous systems to inhibit the growth of microorganisms, the formation of slime in aqueous systems, or the disfigurement or deterioration of substances susceptible to microbiological growth. One example of an N-alkyl heterocyclic compound useful as such a microbicide is N-dodecyl morpholine (DDM). DDM is manufactured by BASF GmbH and by Buckman Laboratories International Inc., Memphis, Tenn.

Preferred N-alkyl heterocyclic compounds for use in the present invention include N-dodecyl morpholine, N-dodecyl imidazole, N-dodecyl-2,6-dimethyl-morpholine, N-dodecyl-5-chloromethyl-2-oxazolidinone, N-dodecyl-2-pyrrolidinone, N-dodecyl hexamethyleneimine, N-dodecyl pyrrolidine, N-dodecyl-3-methyl-piperidine, N-dodecyl piperidine, N-dodecyl-4-methyl-piperidine and N-dodecyl-2-methyl-piperidine. Most preferred of these compounds are N-dodecyl morpholine, (DDM), and N-dodecyl imidazole, (DDI).

Depending on the application, microbicidal compositions according to the present invention may be prepared in various forms known in the art. For example, the composition may be prepared in liquid form as an aqueous solution, dispersion, emulsion, or suspension, a dispersion or suspension in a non-solvent, or as a solution by dissolving the microbicide and the N-alkyl heterocyclic compound in a solvent or combination of solvents. Suitable solvents include, but are not limited to, methyl ethers of glycols, M-pyrol, or petroleum distillates. The microbicidal composition may be prepared as a concentrate for dilution prior to its intended use. Common additives such as surfactants, emulsifiers, dispersants, and the like may be used as known in the art to increase the solubility of the microbicide or N-alkyl heterocyclic compound in a liquid composition or system, such as an aqueous composition or system. In many cases, the biocidal composition of the invention may be solubilized by simple agitation.

Microbicidal compositions of the present invention may also be prepared in solid form, for example as a powder or tablet, using means known in the art. In a preferred method of preparation, a liquid product containing the microbicide is deposited on a carrier such as diatomaceous earth or kaolin and mixed with an N-alkyl heterocyclic compound in the form of a liquid or solution to form a powder or tablet.

The microbicide and the N-alkyl heterocyclic compound may be combined in a single composition. Alternatively, the microbicide and the N-alkyl heterocyclic compound may be employed as separate components such that combined amount for the intended use is effective to control the growth of at least one microorganism.

As discussed above, the invention, the N-alkyl heterocyclic compound potentiates, or even synergistically enhances, the microbicidal effect of the microbicide. Thus, combining an N-alkyl heterocyclic compound with a micrqbicide provides superior microbicidal activity to control the growth of microorganisms as compared to the microbicidal capability of the microbicide alone.

According to the present invention, control of the growth of a microorganism on a substrate or in an aqueous system means control to, at, or below a desired level and for a desired period of time for the particular substrate or system. This can vary from the complete prevention or inhibition of microbiological growth to control at a certain desired level and for a desired time. The combination of microbicide and N-alkyl heterocyclic compound described here can, in many cases, reduce the total microbiological count to undetectable limits and maintain the count at that level for a significant period of time. Accordingly, the combination may be used to preserve a substrate or system.

The effective amount or percentage of the combination of a microbicide and an N-alkyl heterocyclic compound necessary to achieve the desired result will vary somewhat depending on the substrate or aqueous system to be protected, the conditions for microbial growth, the particular microbicide, and the degree of protection desired. For a particular application, the amount of choice may be determined by routine testing of various amounts prior to treatment of the entire affected substrate or system. In general, an effective amount used on a substrate ranges from about 0.0001% to about 4% (w/w); preferably about 0.0001% to about 0.2%. With aqueous systems, an effective amount may range from about 0.5 to about 5000 parts per million, more preferably from about 5 to about 1000 parts per million of the aqueous system, and most preferably from, about 10 to about 25 parts per million. Similar amounts effectively control slime formation. For slime control, effective amounts preferably range from about 1 to about 200 parts per million, and more preferably, from about 1 to about 25 parts per million of the aqueous system.

In a preferred embodiment, combinations of a microbicide and an N-alkyl heterocyclic compound are those combinations having a weight ratio of microbicide to N-alkyl heterocyclic compound from about 99:1 to about 1:99. More preferably the weight ratio is from about 60:10 to about 10:60, and most preferably, from about 50:50 to about 25:75. The weight ratio may vary depending on the microbicide, the intended use, the microorganism encountered as well as the particular material, product, or system to which the combination according to the invention is applied.

The combination of a microbicide and an N-alkyl heterocyclic compound may be applied in a variety of industrial uses and processes for microorganism control. The combination may be used in place of and in the same manner as other microbicides traditionally used in the particular industry. As discussed above, such industries include, but are not limited to, the leather industry, the lumber industry, the papermaking industry, the textile industry, the agricultural industry, and the coating industry. The combination of a microbicide and an N-alkyl heterocyclic compound may also be used with aqueous systems such as those previously discussed which are subject to microbiological attack and degradation. The problems caused by microbiological attack and deterioration in these various applications has been described above. The use of the combination of a microbicide and an N-alkyl heterocyclic compound according to the invention to control the growth of microorganisms in particular exemplary applications is described below.

The invention also relates to a method for controlling the growth of microorganisms on various substrates. The method comprises the step of contacting a substrate susceptible to microbiological growth or attack with a microbicide and an N-alkyl heterocyclic compound, as described above. The microbicide and N-alkyl heterocyclic compound are present in a combined amount effective to control the growth of at least one microorganism on the substrate. Preferably, the method may be used to eliminate or prevent substantially all microbiological growth on the substrate. As discussed above, the microbicide and the N-alkyl heterocyclic compound may be applied together or as separate compositions. Preferred applications of this general method are discussed below.

In the leather industry, the combination of a microbicide and an N-alkyl heterocyclic compound may be used to control the growth of microorganisms on a hide during a tanning process. To achieve this control, the hide is contacted with a combined amount of a microbicide and an N-alkyl heterocyclic compound effective to control the growth of at least one microorganism on the hide. The combination of the microbicide and the N-alkyl heterocyclic compound may be used in the tanning process in similar amounts and manner similar to that used to apply other microbicides used in the tanning industry. The type of hide may be any type of hide or skin that is tanned, for example cowhide, snake skin, alligator skin, sheep skin, and the like. The amount used, to some extent, will depend on the degree of microbiological resistance required and may be readily determined by one skilled in the art.

A typical tanning process comprises a number of stages, including, but not limited to, a pickling stage, a chrome-tanning stage, a vegetable-tanning stage, a post-tan washing stage, a retaining stage, a dyeing stage, and a fatliquoring stage. The combination of a microbicide and an N-alkyl heterocyclic compound may be used during all process stages in the tanning process in addition to those stages where a known microbiological problem is occurring. In each stage, the combination of a microbicide and an N-alkyl heterocyclic compound may be a component of the appropriate tanning liquor applied to the hide undergoing tanning.

Incorporating the microbicide and an N-alkyl heterocyclic compound in a tanning liquor protects the hide from microbiological deterioration during the tanning process. Preferably, the combination is uniformly dispersed, e.g., under agitation, into an appropriate liquor to be used in a tanning process. Typical tanning liquors include, for example, a pickling liquor, a chrome-tanning liquor, a vegetable-tanning liquor, a post-tan washing liquor, a retaining liquor, a dye liquor, and a fatliquor. This method of application ensures that the combination applied to the hides protects against microbiological attack, deterioration, or other microbiological degradation.

In a somewhat analogous nature, the combination of the invention may also be employed to control the growth of microorganisms on a textile substrate in a textile manufacturing process. Contacting the textile substrate with a combination of a microbicide and an N-alkyl heterocyclic compound according to the invention effectively controls the growth of a microorganism on the textile substrate. In a textile process, the combination may be used in similar amounts and a manner similar to other microbicides commonly used in such processes. As one of ordinary skill would appreciate, particular amounts generally depend on the textile substrate and the degree of microbiological resistance required.

The step of contacting the textile substrate with the combination of a microbicide and an N-alkyl heterocyclic compound may be accomplished using means known in the textile art. To control microbiological growth, a textile process generally dips the textile substrate into a bath containing a microbicide, alone or with other chemicals used to treat the textile substrate. Alternatively, the textile substrate may be sprayed with a formulation containing a microbicide. In the bath or the spray, the combination of microbicide and N-alkyl heterocyclic compound according to the invention are present in a combined amount effective to control the growth of at least one microorganism on the textile substrate. Preferably, the bath and the spray are aqueous-based compositions.

To preserve the value of its raw materials and products, the lumber industry also must control the growth of microorganisms in order to prevent microbiological degradation of lumber. The combination of a microbicide and an N-alkyl heterocyclic compound according to the invention is effective to control the growth of microorganisms on lumber.

The combination of a microbicide and an N-alkyl heterocyclic compound may be used to protect the lumber in similar amounts and a similar manner employed for other microbicides used in the lumber industry. Contacting lumber with an effective amount of the combination may be accomplished, for example, by spraying the lumber with an aqueous formulation containing the combination of a microbicide and an N-alkyl heterocyclic compound, by dipping the lumber into a dip bath containing the combination, or other means known in the art. Dipping the lumber in an aqueous bath is preferred.

The microbicide and the N-alkyl heterocyclic compound are preferably uniformly dispersed in a bath (for example, by agitation) prior to the dipping of the lumber into the bath. In general, the lumber is dipped into the bath, raised, allowed to drip dry, and then air dried. The dip time will depend, as is known in the art, on a variety of factors such as the microbicide, the degree of microbiological resistance desired, the moisture content of the lumber, type and density of the wood, etc. Pressure may be applied to promote penetration of the combination into the lumber being treated. Applying a vacuum to the upper surface of the lumber may also be used to degas the lumber and promote increased wetting of the lumber by a bath containing the microbicidal combination.

The combination of a microbicide and an N-alkyl heterocyclic compound according to the invention also has uses in the agricultural industry. To control the growth of microorganisms on a seed or plant, the seed or plant may be contacted with a microbicide and an N-alkyl heterocyclic compound in a combined amount effective to control the growth of at least one microorganism on the seed or plant. This contacting step may be accomplished using means and amounts known in the agricultural industry for other microbicides. For example, the seed or plant may be sprayed with an aqueous formulation containing the combination of microbicide and N-alkyl heterocyclic compound, or dipped into a bath containing the combination. After being sprayed or dipped, the seed or plant is generally dried by means known in the art such as drip drying, heated drying, or air drying. For plants or crops, the combination may also be applied using a soil drench. Soil drenching is particularly advantageous when the microorganisms of concern inhabit the soil surrounding the plant.

Yet another aspect of the present invention is a method for controlling the growth of microorganisms in an aqueous system capable of supporting such growth. The aqueous system is treated with a microbicide and an N-alkyl heterocyclic compound such that the microbicide and N-alkyl heterocyclic compound are present in a combined amount effective to control the growth of at least one microorganism in the aqueous system. This includes controlling, and preferably preventing, slime formation in the aqueous system.

Examples of various aqueous systems include, but are not limited to, latexes, surfactants, dispersants, stabilizers, thickeners, adhesives, starches, waxes, proteins, emulsifying agents, cellulose products, aqueous emulsions, aqueous detergents, coating compositions, paint compositions, alum compositions, and resins formulated in aqueous solutions, emulsions or suspensions. The combination may also be employed in aqueous systems used in industrial processes such as metal working fluids, cooling waters (both intake cooling water and effluent cooling water), and waste waters including waste waters or sanitation waters undergoing treatment of the waste in the water, e.g. sewage treatment.

As with the other uses discussed above, the combination of the invention may be used in the same amounts and in the same manner as microbicides traditionally used in these various aqueous systems. The combination not only protects the aqueous system prior to use or when stored, but in many cases protects the aqueous system when in use or in appropriate applications even after the aqueous system has dried. When used in a paint formulation for example, the combination not only protects the paint in the can, but also the paint film after being applied to a substrate.

Another embodiment of the present invention is a method for controlling the growth of microorganisms on paper or in a papermaking process, e.g., in a pulp or paper slurry and on a finished paper product such as paper board. The paper, pulp, or slurry is contacted with a microbicide and an N-alkyl heterocyclic compound in a combined amount effective to control the growth of at least one microorganism on the paper, the pulp or in a slurry. The contacting step is accomplished using means and amounts known in the papermaking art.

According to this aspect of the invention, for example, a forming web on a papermaking machine (or a wet-lap pulp) may be contacted with the combination of a microbicide and an N-alkyl heterocyclic compound by spraying an aqueous dispersion containing the microbicide and N-alkyl heterocyclic compound onto the pulp after the pulp leaves the presses in a papermaking process. Or, the microbicide and the N-alkyl heterocyclic compound may be incorporated into a bath used at the wet or size press and the web contacted by nipping the web to incorporate the combination into the web with any other agents applied at the press. Alternatively, the pulp may be contacted by mixing the microbicide and N-alkyl heterocyclic compound into the pulp/white water mixture, preferably prior to the pulp reaching the formation wire.

When treating paper (which includes paperboard and other cellulosic products or substrates), the microbicide and N-alkyl heterocyclic compound may be added into pulp slurries in the headbox, in the substrate forming solution, or in the white water system to treat the water system itself or for incorporation into the body of the paper. Alternatively, as with other known microbicides, the combination of a microbicide and an N-alkyl heterocyclic compound according to the invention may be mixed into a coating used to coat the finished paper.

The activity of the combinations described above has been confirmed using standard laboratory techniques as discussed below. In many cases, the N-alkyl heterocyclic compound potentiates, or even synergistically enhances, the microbicidal affect of the particular microbicide. The following examples are intended to illustrate, not limit, the present invention.

EXAMPLES

One procedure for determining a potentiating, or even synergistic, interaction between two compounds utilizes the same technique and apparatus as that used in the basic determination of antifungal activity for a single compound. However, the identification of an interaction between two compounds requires a special arrangement of treatments in an experimental design known as a "factorial" arrangement. This is commonly accomplished using a "checkerboard" design in which each vertical column represents a different concentration of Compound A, and each horizontal row represents a different concentration of Compound B. The concentration series for each compound alone begins at "zero". Thus, the correct factorial design provides:

(a) a "no chemical" control (position row 1, column 1), (b) results for the concentration series of each chemical alone (on row 1: chemical B=0, thus chemical A is in a series by itself; on column 1, compound A=0, thus compound B is in a series by itself), and (c) each concentration of compound A in a combination with each concentration of compound B.

In the procedure, each position in the factorial or checkerboard design is occupied by a culture tube containing 5 ml of sterile liquid culture medium. Individual stock solutions for both compounds are prepared, and the appropriate volume (µl) is added to the medium to achieve the required concentration specified by the test protocol. Each tube is inoculated with 100 µl of spore suspension prepared from the test fungus (*Aspergillus niger*). The suspension is prepared by swabbing the surface of a viable culture (agar slant) and introducing the collected spores into a bottle containing 100 ml of sterile water. The spore suspension is complete when the optical density=0.28 at 686 nm. The inoculated treatments are incubated in the dark at 28° C. for seven days. All tubes then are observed for either the presence or absence of fungal mat growing on the surface of the liquid medium.

The key items of data recorded are:

(1) the lowest concentration (minimum inhibitory concentration, MIC) of each test compound separately for which there was no growth, and (2) the lowest concentration of compound A in combination with compound B for which there was no growth.

The above procedure was used to determine the potentiating effect of an N-alkyl heterocyclic compound with various microbicides. Tables 1–12 show the results of the various tests and the potentiation of microbicidal effect using an N-alkyl heterocyclic compound. Tables 1–12 present both the lowest concentrations of each test compound separately for which there was no growth, and the lowest concentration of compound A in combination with compound B for which there was no growth. A plus (+) sign represents the presence of fugal mat and a minus (−) sign represents the absence of fungal mat. The following compounds or formulations were used:

dodecyl morpholine (DDM), technical grade 85–95% pure;

dodecyl imidazole (DDI), technical grade 85–95% pure;

Kathon, Busan® 1078 product, Buckman Laboratories Inc., Memphis, Tenn.;

Bronopol;

iodopropargyl butyl carbamate (IPBC), technical grade 95% pure;

iodopropargyl carbamate (IPC), technical grade 95% pure;

2,2-Dibromo-3-nitrilopropionamide (DBNPA), Busan® 94 product, Buckman Laboratories Inc., Memphis, Tenn.;

tribromophenol, GREAT LAKES PH-73 product, Great Lakes Chemical, West Lafayette, Ind.; and 1,2-benzisothiazoline-3-one, Proxel GXL-20, ICI Specialty Chemicals;

TABLE 1

Tribromophenol (compound A) and DDM (compound B)

| | | | | | | | | | | | | B |
|---|---|---|---|---|---|---|---|---|---|---|---|---|
| − | − | − | − | − | − | − | − | − | − | − | − | 1280 |
| − | − | − | − | − | − | − | − | − | − | − | − | 640 |
| − | − | − | − | + | + | + | + | + | + | + | + | 320 |
| − | − | − | + | + | + | + | + | + | + | + | + | 160 |
| − | − | − | + | + | + | + | + | + | + | + | + | 80 |
| − | − | − | + | + | + | + | + | + | + | + | + | 40 |
| − | − | − | + | + | + | + | + | + | + | + | + | 20 |
| − | − | − | + | + | + | + | + | + | + | + | + | 0 |
| A | 640 | 320 | 160 | 80 | 40 | 20 | 10 | 5 | 2.5 | .25 | .625 | .0 |

TABLE 2

Bronopol (compound A) and DDM (compound B)

| | | | | | | | | | | | | B |
|---|---|---|---|---|---|---|---|---|---|---|---|---|
| − | − | − | − | − | − | − | − | − | − | − | − | 1280 |
| − | − | − | − | − | − | − | − | − | − | − | − | 640 |
| − | − | − | + | + | + | + | + | + | + | + | + | 320 |
| − | − | − | + | + | + | + | + | + | + | + | + | 160 |
| − | − | − | + | + | + | + | + | + | + | + | + | 80 |
| − | − | − | + | + | + | + | + | + | + | + | + | 40 |
| − | − | − | + | + | + | + | + | + | + | + | + | 20 |
| − | − | + | + | + | + | + | + | + | + | + | + | 0 |
| A | 160 | 80 | 40 | 20 | 10 | 5 | 2.5 | 1.25 | .625 | .313 | .156 | 0 |

TABLE 3

IPBC (compound A) and DDM (compound B)

| | | | | | | | | | | | | B |
|---|---|---|---|---|---|---|---|---|---|---|---|---|
| − | − | − | − | − | − | − | − | − | − | − | − | 1280 |
| − | − | − | − | − | − | − | − | − | − | − | − | 640 |
| − | − | + | + | + | + | + | + | + | + | + | + | 320 |
| − | − | + | + | + | + | + | + | + | + | + | + | 160 |
| − | − | + | + | + | + | + | + | + | + | + | + | 80 |
| − | + | + | + | + | + | + | + | + | + | + | + | 40 |
| − | + | + | + | + | + | + | + | + | + | + | + | 20 |
| − | + | + | + | + | + | + | + | + | + | + | + | 0 |
| A | 640 | 320 | 160 | 80 | 40 | 20 | 10 | 5 | 2.5 | 1.25 | .625 | 0 |

TABLE 4

IPC (compound A) and DDM (compound B)

| | | | | | | | | | | | | B |
|---|---|---|---|---|---|---|---|---|---|---|---|---|
| − | − | − | − | − | − | − | − | − | − | − | − | 1280 |
| − | − | − | − | + | + | + | + | + | + | + | + | 640 |
| − | − | − | − | + | + | + | + | + | + | + | + | 320 |
| − | − | − | − | + | + | + | + | + | + | + | + | 160 |
| − | − | − | − | + | + | + | + | + | + | + | + | 80 |
| − | − | − | + | + | + | + | + | + | + | + | + | 40 |
| − | − | − | + | + | + | + | + | + | + | + | + | 20 |
| − | − | − | + | + | + | + | + | + | + | + | + | 0 |
| A | 640 | 320 | 160 | 80 | 40 | 20 | 10 | 5 | 2.5 | 1.25 | .625 | 0 |

TABLE 5

Kathon (compound A) and DDM (compound B)

| | | | | | | | | | | | | B |
|---|---|---|---|---|---|---|---|---|---|---|---|---|
| − | − | − | − | − | − | − | − | − | − | − | − | 1280 |
| − | − | − | − | − | − | − | − | − | − | − | − | 640 |
| − | − | − | + | + | + | + | + | + | + | + | + | 320 |
| − | − | − | + | + | + | + | + | + | + | + | + | 160 |
| − | − | − | + | + | + | + | + | + | + | + | + | 80 |
| − | − | − | + | + | + | + | + | + | + | + | + | 40 |
| − | − | − | + | + | + | + | + | + | + | + | + | 20 |
| − | − | − | + | + | + | + | + | + | + | + | + | 0 |
| A | 160 | 80 | 40 | 20 | 10 | 5 | 2.5 | .625 | .313 | .156 | .078 | 0 |

TABLE 6

DBNPA (compound A) and DDM (compound B)

| | | | | | | | | | | | | B |
|---|---|---|---|---|---|---|---|---|---|---|---|---|
| − | − | − | − | − | − | − | − | − | − | − | − | 1280 |
| − | − | − | − | − | − | − | − | − | − | − | − | 640 |
| − | − | − | + | + | + | − | + | + | + | + | + | 320 |
| − | − | + | + | + | + | + | + | + | + | + | + | 160 |
| − | − | + | + | + | + | + | + | + | + | + | + | 80 |
| − | − | + | + | + | + | + | + | + | + | + | + | 40 |
| − | + | + | + | + | + | + | + | + | + | + | + | 20 |
| − | + | + | + | + | − | + | + | + | + | + | + | 0 |
| A | 64 | 32 | 16 | 8 | 4 | 2 | 1 | 0.5 | 0.25 | 0.125 | 0.06 | 0 |

TABLE 7

Kathon (compound A) and DDI (compound B)

| A → | 640 | 320 | 160 | 80 | 40 | 20 | 10 | 5 | 2.5 | 1.25 | .625 | 0 | B |
|---|---|---|---|---|---|---|---|---|---|---|---|---|---|
| | − | − | − | − | − | − | − | − | − | − | − | − | 160 |
| | − | − | − | − | − | − | − | − | − | − | − | − | 80 |
| | − | − | − | − | − | − | − | − | − | − | + | + | 40 |
| | − | − | − | − | − | − | − | + | + | + | + | + | 20 |
| | − | − | − | − | − | − | + | + | + | + | + | + | 10 |
| | − | − | − | − | − | + | + | + | + | + | + | + | 5 |
| | − | − | − | − | − | + | + | + | + | + | + | + | 2.5 |
| | − | − | − | − | − | + | + | + | + | + | + | + | 0 |

TABLE 8

Bronopol (compound A) and DDI (compound B)

| A → | 160 | 80 | 40 | 20 | 10 | 5 | 2.5 | 1.25 | .625 | .312 | .156 | 0 | B |
|---|---|---|---|---|---|---|---|---|---|---|---|---|---|
| | − | − | − | − | − | − | − | − | − | − | − | − | 160 |
| | − | − | − | − | − | − | − | − | − | − | − | − | 80 |
| | − | − | − | − | − | − | − | − | − | − | − | − | 40 |
| | − | − | − | − | − | − | + | + | + | + | + | + | 20 |
| | − | − | − | − | + | + | + | + | + | + | + | + | 10 |
| | − | − | − | + | + | + | + | + | + | + | + | + | 5 |
| | − | − | − | + | + | + | + | + | + | + | + | + | 2.5 |
| | − | − | − | + | + | + | + | + | + | + | + | + | 0 |

TABLE 9

IPBC (compound A) and DDI (compound B)

| A → | 640 | 320 | 160 | 80 | 40 | 20 | 10 | 5 | 2.5 | 1.25 | .625 | 0 | B |
|---|---|---|---|---|---|---|---|---|---|---|---|---|---|
| | − | − | − | − | − | − | − | − | − | − | − | − | 160 |
| | − | − | − | − | − | − | − | − | − | − | − | − | 80 |
| | − | − | − | − | − | − | − | + | + | + | + | + | 40 |
| | − | − | − | − | − | + | + | + | + | + | + | + | 20 |
| | − | − | − | + | + | + | + | + | + | + | + | + | 10 |
| | − | − | + | + | + | + | + | + | + | + | + | + | 5 |
| | − | − | + | + | + | + | + | + | + | + | + | + | 2.5 |
| | − | − | + | + | + | + | + | + | + | + | + | + | 0 |

TABLE 10

IPC (compound A) and DDI (compound B)

| A → | 640 | 320 | 160 | 80 | 40 | 20 | 10 | 5 | 2.5 | 1.25 | .625 | 0 | B |
|---|---|---|---|---|---|---|---|---|---|---|---|---|---|
| | − | − | − | − | − | − | − | − | − | − | − | − | 160 |
| | − | − | − | − | − | − | − | − | − | − | − | − | 80 |
| | − | − | − | − | − | − | − | − | + | + | + | + | 40 |
| | − | − | − | − | − | − | + | + | + | + | + | + | 20 |
| | − | − | − | − | + | + | + | + | + | + | + | + | 10 |
| | − | − | − | + | + | + | + | + | + | + | + | + | 5 |
| | − | − | − | + | + | + | + | + | + | + | + | + | 2.5 |
| | − | − | + | + | + | + | + | + | + | + | + | + | 0 |

TABLE 11

Tribromophenal (compound A) and DDI (compound B)

| | | | | | | | | | | | | B |
|---|---|---|---|---|---|---|---|---|---|---|---|---|
| − | − | − | − | − | − | − | − | − | − | − | − | 160 |
| − | − | − | − | − | − | − | − | − | − | − | − | 80 |
| − | − | − | − | + | + | + | + | + | + | + | + | 40 |
| − | − | − | − | + | + | + | + | + | + | + | + | 20 |
| − | − | − | + | + | + | + | + | + | + | + | + | 10 |
| − | − | + | + | + | + | + | + | + | + | + | + | 5 |
| − | − | + | + | + | + | + | + | + | + | + | + | 2.5 |
| − | − | + | + | + | + | + | + | + | + | + | + | 0 |
| A | 640 | 320 | 160 | 80 | 40 | 20 | 10 | 5 | 2.5 | 1.25 | .625 | 0 |

TABLE 12

Proxel GXL-20 (compound A) and DDI (compound B)

| | | | | | | | | | | | | B |
|---|---|---|---|---|---|---|---|---|---|---|---|---|
| − | − | − | − | − | − | − | − | − | − | − | − | 160 |
| − | − | − | − | − | − | − | − | − | − | − | − | 80 |
| − | − | − | − | − | − | + | − | + | − | − | − | 40 |
| − | − | − | − | + | + | + | + | + | + | + | + | 20 |
| − | − | + | + | + | + | + | + | + | + | + | + | 10 |
| − | + | + | + | + | + | + | + | + | + | + | + | 5 |
| − | + | + | + | + | + | + | + | + | + | + | + | 2.5 |
| − | + | + | + | + | + | + | + | + | + | + | + | 0 |
| A | 320 | 160 | 80 | 40 | 20 | 10 | 5 | 2.5 | 1.25 | .625 | .3125 | 0 |

The claimed invention is:

1. A method to increase the effectiveness of a microbicide comprising the step of applying at least one microbicide and an N-alkyl heterocyclic compound to a substrate or aqueous system subject to the growth of microorganisms, wherein the N-alkyl heterocyclic compound has the formula:

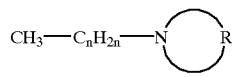

in which n varies from 5 to 17 and the heterocyclic ring defined by

is a substituted or unsubstituted ring having four to eight members and the N-alkyl heterocyclic compound is applied in an amount effective to potentiate the microbicidal activity of the microbicide.

2. A method according to claim 1, wherein the N-alkyl heterocyclic compound is N-dodecyl morpholine.

3. A method according to claim 1, wherein the N-alkyl heterocyclic compound is N-dodecyl imidazole.

4. A microbicidal composition comprising:

(a) at least one microbicide and (b) an N-alkyl heterocyclic compound of the formula:

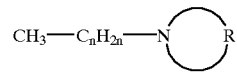

wherein n varies from 5 to 17, the heterocyclic ring defined by

is a substituted or unsubstituted ring having four to eight members, and wherein (a) and (b) are present in a combined amount effective to control the growth of at least one microorganism and the N-alkyl heterocyclic compound (b) is present in an amount effective to potentiate the microbicidal activity of the microbicide (a).

5. A microbicidal composition according to claim 4, wherein the N-alkyl heterocyclic compound is N-dodecyl morpholine and the microorganism is selected from algae, fungi, and bacteria.

6. A microbicidal composition according to claim 4, wherein the N-alkyl heterocyclic compound is N-dodecyl imidazole and the microorganism is selected from algae, fungi, and bacteria.

7. A microbicidal composition according to claim 4, wherein the composition is an aqueous formulation.

8. A method for controlling the growth of microorganisms on a substrate comprising the step of contacting a substrate susceptible to the growth of microorganisms with (a) at least one microbicide, and (b) an N-alkyl heterocyclic compound of the formula:

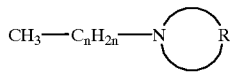

wherein n may be from 5 to 17, the heterocyclic ring defined by

is a substituted or unsubstituted ring having four to eight members, and wherein (a) and (b) are present in a combined amount effective to control the growth of at least one microorganism on the substrate and the N-alkyl heterocyclic compound (b) is present in an amount effective to potentiate the microbicidal activity of the microbicide (a).

9. A method according to claim 8, wherein the N-alkyl heterocyclic compound is N-dodecyl morpholine and the microorganism is selected from algae, fungi, and bacteria.

10. A method according to claim 8, wherein the N-alkyl heterocyclic compound is N-dodecyl imidazole, and the microorganism is selected from algae, fungi, and bacteria.

11. A method of claim 8 wherein the substrate is a hide, a textile substrate, lumber, a seed, or a plant.

12. A method for controlling the growth of microorganisms in an aqueous system capable of supporting growth of a microorganism comprising the step of treating the aqueous system with
(a) at least one microbicide, and
(b) an N-alkyl heterocyclic compound of the formula:

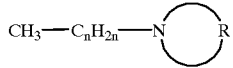

wherein n varies from 5 to 17, the heterocyclic ring defined by

is a substituted or unsubstituted ring having four to eight members, and wherein (a) and (b) are present in a combined amount effective to control the growth of at least one microorganism and the N-alkyl heterocyclic compound (b) is present in an amount effective to potentiate the microbicidal activity of the microbicide (a).

13. A method according to claim 12, wherein the N-alkyl heterocyclic compound is N-dodecyl morpholine and the microorganism is selected from algae, fungi, and bacteria.

14. A method according to claim 12, wherein the N-alkyl heterocyclic compound is N-dodecyl imidazole, and the microorganism is selected from algae, fungi, and bacteria.

15. A method according to claim 12, wherein said aqueous system is selected from the group consisting of a latex, a metal working fluid, an aqueous emulsion, an aqueous detergent, cooling water, and an aqueous resin formulation.

16. A method for controlling the growth of microorganisms on pulp or paper in a papermaking process, comprising the step of contacting the pulp or paper with
(a) at least one microbicide, and
(b) an N-alkyl heterocyclic compound of the formula:

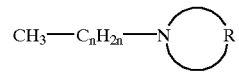

wherein n varies from 5 to 17, the heterocyclic ring defined by N R is a substituted or unsubstituted ring having four to eight members, and (a) and (b) are present in a combined amount effective to control the growth of at least one microorganism and the N-alkyl heterocyclic compound (b) is present in an amount effective to potentiate the microbicidal activity of the microbicide (a).

17. A method according to claim 16, wherein the pulp is contacted by mixing the microbicide and an N-alkyl heterocyclic compound into a pulp slurry prior to reaching a formation wire in a papermaking process.

18. A method according to claim 16, wherein the N-alkyl heterocyclic compound is N-dodecyl morpholine and the microorganism is selected from algae, fungi, and bacteria.

19. A method according to claim 16, herein the N-alkyl heterocyclic compound is N-dodecyl imidazole, and the microorganism is selected from algae, fungi, and bacteria.

* * * * *

UNITED STATES PATENT AND TRADEMARK OFFICE
CERTIFICATE OF CORRECTION

PATENT NO. : 6,034,081
DATED : March 7, 2000
INVENTOR(S) : Whittemore et al.

It is certified that error appears in the above-identified patent and that said Letters Patent is hereby corrected as shown below:

ABSTRACT,
Line 9, replace "In" with -- N --.

Column 17,
Line 59, after "microbicide" insert -- , wherein the microbicide is selected from 5-chloro-2-methyl-4-isothiazolin-3-one, 2-methyl-4-isothiazolin-3-one, 2-bromo-2-nitropropane-1,3-diol, iodopropargyl butyl carbamate, iodopropargyl carbamate, 2,2-dibromo-3-nitrilopropionamide, tribromophenol and 1,2-benzisothiazoline-3-one, and mixtures thereof, and the N-alkyl heterocyclic compound is selected from N-dodecyl morpholine, N-dodecyl imidazole, N-dodecyl-2,6-dimethyl-morpholine, N-dodecyl-5-chloromethyl-2-oxazolidinone, N-dodecyl-2- pyrrolidinone, N-dodecyl hexamethyleneimine, N-dodecyl pyrrolidine, N-dodecyl-3-methylpiperidine, N-dodecyl-piperidine, N-dedocyl-4-methyl-piperidine and N-dodecyl-2-methyl-piperidine --.

Column 18,
Line 52, after "microbicide (a)" insert -- , wherein the microbicide is selected from 5-chloro-2-methyl-4-isothiazolin-3-one, 2-methyl-4-isothiazolin-3-one, 2-bromo-2-nitropropane-1,3-diol, iodopropargyl butyl carbamate, iodopropargyl carbamate, 2,2-dibromo-3-nitrilopropionamide, tribromophenol and 1,2-benzisothiazoline-3-one, and mixtures thereof, and the N-alkyl heterocyclic compound is selected from N-dodecyl morpholine, N-dodecyl imidazole, N-dodecyl-2,6-dimethyl-morpholine, N-dodecyl-5- chloromethyl-2-oxazolidinone, N-dodecyl-2- pyrrolidinone, N-dodecyl hexamethyleneimine, N-dodecyl pyrrolidine, N-dodecyl-3-methylpiperidine, N-dodecyl-piperidine, N-dedocyl-4-methyl-piperidine and N-dodecyl-2-methyl-piperidine --.

UNITED STATES PATENT AND TRADEMARK OFFICE
CERTIFICATE OF CORRECTION

PATENT NO. : 6,034,081
DATED : March 7, 2000
INVENTOR(S) : Whittemore et al.

It is certified that error appears in the above-identified patent and that said Letters Patent is hereby corrected as shown below:

Column 19,
Line 21, after "microbicide (a)" insert -- , wherein the microbicide is selected from 5-chloro-2-methyl-4-isothiazolin-3-one, 2-methyl-4-isothiazolin-3-one, 2-bromo-2-nitropropane-1,3-diol, iodopropargyl butyl carbamate, iodopropargyl carbamate, 2,2-dibromo-3-nitrilopropionamide, tribromophenol and 1,2-benzisothiazoline-3-one, and mixtures thereof, and the N-alkyl heterocyclic compound is selected from N-dodecyl morpholine, N-dodecyl imidazole, N-dodecyl-2,6-dimethyl-morpholine, N-dodecyl-5- chloromethyl-2-oxazolidinone, N-dodecyl-2- pyrrolidinone, N-dodecyl hexamethyleneimine, N-dodecyl pyrrolidine, N-dodecyl-3-methylpiperidine, N-dodecyl-piperidine, N-dedocyl-4-methyl-pipendine and N-dodecyl-2-methyl-piperidine --.

Column 20,
Line 5, after "microbicide (a)" insert -- , wherein the microbicide is selected from 5-chloro-2-methyl-4-isothiazolin-3-one, 2-methyl-4-isothiazolin-3-one, 2-bromo-2-nitropropane-1,3-diol, iodopropargyl butyl carbamate, iodopropargyl carbamate, 2,2-dibromo-3-nitrilopropionamide, tribromophenol and 1,2-benzisothiazoline-3-one, and mixtures thereof, and the N-alkyl heterocyclic compound is selected from N-dodecyl morpholine, N-dodecyl imidazole, N-dodecyl-2,6-dimethyl-morpholine, N-dodecyl-5- chloromethyl-2-oxazolidinone, N-dodecyl-2- pyrrolidinone, N-dodecyl hexamethyleneimine, N-dodecyl pyrrolidine, N-dodecyl-3-methylpiperidine, N-dodecyl-piperidine, N-dedocyl-4-methyl-piperidine and N-dodecyl-2-methyl-piperidine --.
Line 37, after "microbicide (a)" insert -- , wherein the microbicide is selected from 5-chloro-2-methyl-4-isothiazolin-3-one, 2-methyl-4-isothiazolin-3-one, 2-bromo-2-nitropropane-1,3-diol, iodopropargyl butyl carbamate, iodopropargyl carbamate, 2,2-dibromo-3-nitrilopropionamide, tribromophenol and 1,2-benzisothiazoline-3-one, and mixtures thereof, and the N-alkyl heterocyclic compound is selected from N-dodecyl morpholine, N-dodecyl imidazole, N-dodecyl-2,6-dimethyl-morpholine, N-dodecyl-5- chloromethyl-2-oxazolidinone, N-dodecyl-2- pyrrolidinone, N-dodecyl hexamethyleneimine, N-dodecyl pyrrolidine, N-dodecyl-3-methylpiperidine, N-dodecyl-piperidine, N-dedocyl-4-methyl-piperidine and N-dodecyl-2-methyl-piperidine --.

UNITED STATES PATENT AND TRADEMARK OFFICE
CERTIFICATE OF CORRECTION

PATENT NO. : 6,034,081
DATED : March 7, 2000
INVENTOR(S) : Whittemore et al.

It is certified that error appears in the above-identified patent and that said Letters Patent is hereby corrected as shown below:

Column 20 (continued),
Line 31, replace "N R" with

--.

Signed and Sealed this

Eighth Day of January, 2002

*Attest:*

*Attesting Officer*

JAMES E. ROGAN
*Director of the United States Patent and Trademark Office*